United States Patent [19]

Revici

[11] Patent Number: 4,499,078

[45] Date of Patent: Feb. 12, 1985

[54] METHODS FOR COUNTERACTING THE DELETERIOUS EFFECTS OF SODIUM CHLORIDE

[76] Inventor: Emanuel Revici, 1111 Park Ave., New York, N.Y. 10028

[21] Appl. No.: 487,899

[22] Filed: Apr. 22, 1983

[51] Int. Cl.$^3$ .............................................. A61K 33/14
[52] U.S. Cl. ................................... 424/153; 424/154
[58] Field of Search ................................ 424/154, 153

[56] References Cited

U.S. PATENT DOCUMENTS

| 3,897,550 | 7/1975 | Reynolds | 424/154 X |
| 3,980,773 | 9/1976 | Oh et al. | 424/195 X |
| 3,993,751 | 11/1976 | Zinke | 424/156 X |
| 4,202,887 | 5/1980 | Talbot et al. | 424/154 |

OTHER PUBLICATIONS

Chemical Abstracts, vol. 54, 14592g, (1960), Miksch et al.

Chemical Abstracts, vol. 46, 10448e, (1952), Werle et al.

*Primary Examiner*—Leonard Schenkman
*Assistant Examiner*—Joseph A. Lipovsky
*Attorney, Agent, or Firm*—Pennie & Edmonds

[57] ABSTRACT

A substantially tasteless, non-toxic composition comprising sodium chloride and a magnesium compound containing bivalent negative sulfur and method of using the compositions to control the deleterious effects of large amounts of sodium chloride on the human body.

3 Claims, No Drawings

METHODS FOR COUNTERACTING THE DELETERIOUS EFFECTS OF SODIUM CHLORIDE

FIELD OF THE INVENTION

This invention relates to new and useful improvements in a composition and process for reducing the deleterious effects of ingested sodium chloride and, more particularly, relates to a composition or mixture including sodium chloride and a magnesium compound containing bivalent negative sulfur.

BACKGROUND OF THE INVENTION

It has become apparent in recent years that the ingestion of sodium chloride, especially at the higher levels to which humans have become accustomed, has deleterious effects, mainly related to the cardiovascular system, e.g., high blood pressure and arteriosclerosis, but also encourages growth of tumors. Efforts to restrict the ingestion of salt by eating low or unsalted food or substituting condiments has not been very successful.

DESCRIPTION OF THE INVENTION

A study of the biological activity of compounds has shown that they include either destructive-catabolic or constructive-anabolic actions in the human body. The manifestations of an abnormal condition, as symptoms, signs, pathology analyses and response to therapy are related to this dualism. Hypertension, arteriosclerosis and the growth of tumors are recognized as typical constructive anabolic manifestations. On the other hand, I have shown that the action of compounds upon the body has either an anabolic or a catabolic action. Thus, compounds can be classified as anabolic or catabolic by a series of tests.

By tests, such as of the effect on the second day wound crust pH, or on the curve of the healing of a wound, or on the bloor eosinophile leukocytes and potassium, or on the urine pH, surface tension, specific gravity and chloride excretion, compounds can be established as either anabolic constructive or catabolic destructive.

Through the study from this point of view of the biological actions of the elements, I have shown that the members of the different series (vertical grouping) of the periodic table have either anabolic or catabolic actions. The IA series, to which the sodium belongs, has anabolic actions. The same for the IIIA, VA and VIIA, to which the chloride element belongs. Sodium chloride consequently produces high anabolic effects. Oppositely, I have shown that the series IIA, IVA and VIA have antagonistic catabolic effects.

I have further found that the elements of the same period (horizontal grouping) act at the same level of the body organization, such as subnuclear, nuclear, cellular, metazoic or systemic, and that the sodium and the chloride act at the same metazoic level (tissues and organs). The biological effect of sodium chloride is thus a strong anabolic action at the metazoic level. This explains the noxious action upon the blood pressure and arteries, leading to the anabolic-constructive arteriosclerosis.

Following the same systematization of the elements acting at the same metazoic level as the sodium and chloride but having an opposite catabolic action, it appeared that the use of one or more of the catabolic metazoic elements would produce the opposite action of this biological effect of the sodium chloride.

This was shown to be true experimentally. Magnesium was seen to be opposite biologically to sodium, while the sulfur biologically opposite chlorine. In the case of sulfur, it was found that the bivalent negative was more active than the tetra- and hexa-valent positive.

Based on these primary considerations, compounds having magnesium and sulfur were used, in order to show this antagonism as set forth in the following experiments.

The bilateral adrenalectomy in young rats, of below 150 g, was seen to have almost 100% mortality. The administration of 1% solutions of sodium chloride as drinking water was seen to protect the adrenalectomized animals and, if administered for a sufficient length of time, to prevent the death. The administration together with the sodium chloride of magnesium sulfate, the last in subcutaneous repeated injections of 0.5 ml of a 10% solution for 100 g of animal or orally as 1% in drinking water, was seen to be antagonistic to the action of the sodium chloride. In the adrenalectomized animals treated with sodium chloride and magnesium sulfate the mortality was over 80% instead of almost zero for the adrenalectomized animals receiving only the sodium chloride. The same for the older animals, to which the administration of magnesium sulfate (1% in drinking water) was seen to increase the mortality from 20% in controls to 75% in the animals receiving the magnesium sulfate. The use of the magnesium thiosulfate was still more effective than the magnesium sulfate.

The relationship between sodium chloride, magnesium sulfates and arteriosclerosis was seen in the following experiments.

New Zealand rabbits were given 2 grams of cholesterol a day, orally, together with their food. Sacrificed after one month, they showed atheromatous lesions of the aorta. The animals sacrificed after only two weeks of receiving the cholesterol showed only few minimal lesions or none at all. The addition of sodium chloride (3% to the drinking water) to the animals receiving 2 g of cholesterol daily was seen to induce manifest aorta lesions and this after only two weeks of treatment with cholesterol.

The administration of magnesium thiosulfate at 3%, together with the 3% sodium chloride in the drinking water, was seen to prevent the appearance of the aorta lesions, not only after two weeks as in the controls with NaCl alone, but even after one month.

As noted above, antagonism exists between magnesium and sodium which counteracts the biological action of sodium and that the same antagonism exists between the chlorine and sulfur, especially in the bivalent negative state.

It is thus possible to overcome the adverse effects of sodium chloride by adding various magnesium compounds, such as magnesium oxide or magnesium acetylsalicylate and the sulfur compounds separately. Various sulfur compounds or even colloidal sulfur can be used for this purpose. The ingestation of colloidal sulfur has been found to produce sulfides in the intestines of animals. The bond of magnesium to catabolic sulfur enhances this antisodium action. It has been found that the best results are obtained by utilizing a magnesium compound containing bivalent negative sulfur and especially magnesium thiosulfate.

The composition is prepared by merely mixing sodium chloride with magnesium thiosulfate, preferably previously heated around 170° C. in order to eliminate or reduce its hydrated water. The crystals of magnesium thiosulfate are preferably ground to a fine powder before mixing with sodium chloride. The sodium chloride crystals can also be ground to a fine powder if desired. In this manner the taste of magnesium thiosulfate in the composition is substantially reduced. The amount of magnesium thiosulfate should be at least about 1% by weight of the total composition in order to subsequently antagonize the adverse effects of sodium chloride. Amounts as high as 10% by weight of magnesium thiosulfate can be employed without substantially affecting the taste of the sodium chloride. Amounts as high as 25% by weight could be used where taste is not a factor.

Other catabolic agents, of a lower organizational level of the cells, such as Ca, Sc, V, Mn, Co, Cu, Ge and Se may be added together with the magnesium and sulfur.

Other antianabolic agents, such as vitamins A, D, $B_6$ and $B_{12}$, fatty acids, aldehydes, and the special group of agents having a twin formation (2 atoms with the same electrical charge bound together) can also be added to the magnesium-sulfur agents if desired.

I claim:

1. A method for counteracting the adverse effects of sodium chloride on the human body which comprises administering to said body a composition containing sodium chloride and a magnesium compound containing bivalent negative sulfur where said magnesium compound is present in an amount effective to counteract the adverse effects of said sodium chloride.

2. The method of claim 1 in which the amount of magnesium compound is between about 1 and 10% by weight of the sodium chloride.

3. The method of claim 1 where the magnesium compound is magnesium thiosulfate.

* * * * *